United States Patent [19]

Opgenorth et al.

[11] 4,113,732

[45] Sep. 12, 1978

[54] MANUFACTURE OF BENZOTHIAZOLES

[75] Inventors: Hans-Joachim Opgenorth, Frankenthal; Horst Scheuermann, Ludwigshafen, both of Fed. Rep. of Germany

[73] Assignee: BASF Aktiengesellschaft, Ludwigshafen a. Rhein, Fed. Rep. of Germany

[21] Appl. No.: 810,950

[22] Filed: Jun. 29, 1977

[30] Foreign Application Priority Data

Jul. 10, 1976 [DE] Fed. Rep. of Germany ....... 2631163

[51] Int. Cl.² .......................................... C07D 277/82
[52] U.S. Cl. ................................................... 260/305
[58] Field of Search ........................................ 260/305

[56] References Cited

U.S. PATENT DOCUMENTS

| | | | |
|---|---|---|---|
| 1,987,614 | 1/1935 | Fox | 260/305 |
| 2,055,609 | 9/1936 | Lubs et al. | 260/305 |
| 4,035,379 | 7/1977 | Fuchs | 260/305 |

*Primary Examiner*—Nicholas S. Rizzo
*Attorney, Agent, or Firm*—Johnston, Keil, Thompson & Shurtleff

[57] ABSTRACT

Process for the production of benzothiazoles from N-arylsubstituted thioureas by oxidative ring closure characterized by the use of chlorine as oxidizing agent and by the presence of catalytic amounts of bromine. Yield and quality of the benzothiazoles obtained are very good.

8 Claims, No Drawings

MANUFACTURE OF BENZOTHIAZOLES

The present invention relates to a process for the manufacture of benzothiazoles from compounds of the formula I

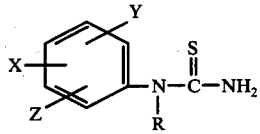

where X is hydrogen, chlorine, bromine, alkyl of 1 to 4 carbon atoms, alkoxycarbonyl of 1 to 4 carbon atoms, alkoxy of 1 to 4 carbon atoms or phenoxy, Y is hydrogen, chlorine, nitro, alkyl of 1 to 4 carbon atoms, alkoxy of 1 to 4 carbon atoms, acetylamino, benzoylamino, methylsulfonyl, ethylsulfonyl, cyano, alkoxycarbonyl (where alkoxy is of 1 to 4 carbon atoms) or sulfamoyl which may or may not be substituted by alkyl of 1 to 4 carbon atoms, Z is hydrogen, chlorine, alkyl of 1 to 4 carbon atoms or alkoxy of 1 to 4 carbon atoms and R is hydrogen, alkyl of 1 to 8 carbon atoms, benzyl or phenylethyl, by oxidative ring closure, in which the ring closure to give the compounds of the formula II

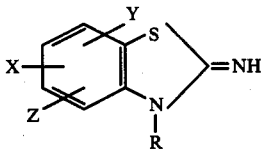

is carried out with chlorine in aprotic organic solvents in the presence of catalytic amounts of bromine or iodine.

Alkyl and alkoxy radicals X, Y and Z are ethyl, propyl, butyl, propoxy and butoxy and especially methyl, methoxy and ethoxy.

Examples of substituted sulfamoyl radicals Y are $SO_2NHCH_3$, $SO_2NHC_2H_5$, $SO_2NHC_3H_7$ or $SO_2NHC_4H_9$, and the corresponding disubstituted radicals.

Examples of suitable aprotic organic solvents for the reaction are chlorohydrocarbons, e.g. methylene chloride, ethylene chloride, chloroform, carbon tetrachloride, trichloroethylene, tetrachloroethylene, chlorobenzene, dichlorobenzene and trichlorobenzene, hydrocarbons, e.g. benzene and cyclohexane, ethers, e.g. tetrahydrofuran, dioxane and glycol dialkyl ethers, and nitrobenzene.

Preferred solvents are chlorobenzene, dichlorobenzene, trichlorobenzene, nitrobenzene, ethylene chloride and chloroform.

For the purpose of the present invention, catalytic amounts of bromine or iodine means amounts of from about $10^{-3}$ to $10^{-1}$ mole, preferably $4 \cdot 10^{-2}$ mole, per mole pound of compound I.

Compounds of the formula I are obtained from compounds of the formula III

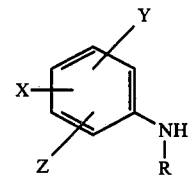

by reaction with an alkali metal thiocyanate or ammonium thiocyanate in the conventional manner. An intermediate stage of isolating the compounds of the formula I before manufacturing the compounds of the formula II by the process of the invention is not necessary.

The ring closure of the compounds of the formula I to give the benzothiazoles requires from about 1 to 1.2 moles, preferably from 1 to 1.05 moles, of chlorine per mole of compound I; it is advantageous to avoid a larger excess.

The reaction according to the invention is advantageously carried out by dissolving or suspending the compound of the formula I in about a 10-fold amount of aprotic solvent, adding bromine and then passing in chlorine. The amount of solvent can vary within wide limits and is chosen from the point of view of the stirrability of the mixture. Advantageous reaction temperatures are from 0° to 80° C., especially from 10° to 60° C. and preferably from 20° to 50° C.

After introducing the chlorine, the mixture is advantageously heated further for from 1 to 2 hours at from 50° to 150° C., preferably from 70° to 100° C.

The benzothiazoles of the formula II are obtained in the form of the hydrochlorides, from which the free benzothiazoles may be prepared in the conventional manner by adding bases.

The process of the invention is of particular importance for the manufacture of compounds of the formula IIa

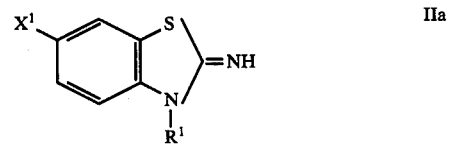

where $X^1$ is hydrogen, chlorine, methyl, ethyl, methoxy, ethoxy, propoxy, butoxy or phenoxy and $R^1$ is hydrogen, alkyl of 1 to 4 carbon atoms, benzyl or phenylethyl.

U.S. Pat. No. 1,984,885 has already disclosed a process for the manufacture of benzothiazoles of the formula II, using chlorine for the ring closure, but this prior process gives products which are additionally chlorinated in the benzo ring.

The use of stoichiometric amounts of bromine (Berichte 36 (1903), 3121 and ibid. 34 (1901), 3130) has also been disclosed, but for economic reasons it is disadvantageous to use bromine.

The process of the invention gives the benzothiazoles of the formula II in outstanding yield and excellent quality, so that the compounds can be converted further, e.g. to dyes, without additional purification in the manner disclosed in U.S. Pat. Nos. 3,101,988 and 2,889,315.

In the Examples which follow, parts and percentages are by weight, unless stated otherwise.

EXAMPLE 1

182 parts of p-methoxyphenyl-thiourea are suspended in 2,200 parts of ethylene chloride. To dehydrate the mixture, 200 parts of the solvent are distilled off under atmospheric pressure. The suspension is cooled to 30° C. and 6 parts of bromine are added. 71 parts of chlorine gas are then passed in over 4 hours at the same temperature, whilst cooling the mixture slightly, and the batch is then refluxed for 1 hour. Thereafter it is allowed to cool to about 70° C. and 1,000 parts of water are hereupon added, causing the solid to dissolve. After removing the organic phase, the ethylene chloride emulsified in the aqueous phase is stripped off in steam. The clear solution is then rendered alkaline, at 50° C., with 130 parts of concentrated ammonia. After the mixture has cooled to room temperature, the precipitate is filtered off, washed neutral with water and dried. The yield is 171 parts of 6-methoxy-2-aminobenzothiazole of melting point 163°–165° C., corresponding to 95% of theory.

EXAMPLE 2

182 parts of p-methoxyphenyl-thiourea are suspended in ethylene chloride, and dehydrated, as described in Example 1. 35.5 parts of chlorine gas are then passed in over 1 hour at 20° C., but without addition of bromine. After stirring for a further hour, 6 parts of bromine are added, the mixture is heated to 40° C., and a further 35.5 parts of chlorine gas are introduced at this temperature over one hour. The reaction product is isolated as described in Example 1. 168 parts of 6-methoxy-2-amino-benzothiazole of melting point 160°–163° C. are thus obtained, corresponding to 93% of theory.

EXAMPLE 3

152 parts of N-phenyl-thiourea in 2,200 parts of ethylene chloride are converted, by the method described in Example 1, to 122 parts (corresponding to a yield of 88% of theory) of 2-amino-benzothiazole of melting point 123°–125° C.

EXAMPLE 4

196 parts of 4-ethoxyphenyl-thiourea in 2,200 parts of ethylene chloride are converted, by the method described in Example 1, to 174 parts (90% of theory) of 6-ethoxy-2-amino-benzothiazole of melting point 161°–163° C.

EXAMPLE 5

186 parts of N-methyl-N-phenyl-thiourea in 700 parts of ethylene chloride are converted, by the method described in Example 1, to 42 parts (88% of theory) of 3-methyl-benzothiazolone-2-imide of melting point 120°–123° C.

EXAMPLE 6

166 parts of N-methyl-N-phenyl-thiourea in 2,200 parts of o-dichlorobenzene are converted, by the method described in Example 1, to 154 parts (94% of theory) of 3-methyl-benzothiazolone-2-imide of melting point 121°–124° C.

EXAMPLE 7

135 parts of N-methylaniline and 115 parts of sodium thiocyanate in 1,600 parts of o-dichlorobenzene are heated to 65°–70° C. whilst adding 10 parts of water. 74 parts of concentrated sulfuric acid are then added dropwise over 2 hours. The mixture is then heated for 3 hours at 100° C. The water is removed by distilling off 200 ml of the solvent. The mixture is then cooled to 30° C., 6 parts of bromine are added, and 98 parts of chlorine gas are passed in at the same temperature. The mixture is then heated for 1 hour at 80° C., after which 1,600 parts of water are added, to the lower phase is separated off and emulsified dichlorobenzene is removed from the aqueous phase by briefly passing steam through it; the aqueous phase is then cooled to 60° C. and about 280 parts of 25% strength ammonia are added. The precipitate is then filtered off, washed with water and dried. The yield is 156 parts (75% of theory) of 3-methyl-benzothiazolone-2-imide of melting point 118°–120° C.

The substituted 2-amino-benzothiazoles shown in the Table which follows are also obtained by methods similar to those described.

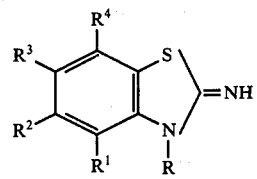

| Example | R¹ | R² | R³ | R⁴ | R | Yield (%) |
|---|---|---|---|---|---|---|
| 8 | OCH₃ | H | OCH₃ | H | H | 91 |
| 9 | H | H | O—C₄H₉ | H | H | 93 |
| 10 | H | H | O—C₆H₅ | H | H | 96 |
| 11 | H | H | —CH₃ | H | H | 95 |
| 12 | H | H | —C₄H₉ | H | H | 91 |
| 13 | CH₃ | H | —Cl | H | H | 97 |
| 14 | H | H | —NH—CO—CH₃ | H | H | 96 |
| 15 | H | H | —NH—CO—C₆H₅ | H | H | 90 |
| 16 | H | H | —OCH₃ | H | —C₈H₁₇ | 69 |
| 17 | H | H | H | H | —CH₂—C₆H₅ | 73 |
| 18 | H | H | H | H | —C₂H₄—C₆H₅ | 58 |
| 19 | H | H | —SO₂CH₃ | H | H | 73 |
| 20 | H | H | CO—OC₂H₅ | H | H | 84 |
| 21 | H | CO—OCH₃ | H | CO—OCH₃ | H | 55 |
| 22 | —OCH₃ | H | —OCH₃ | Cl | H | 89 |
| 23 | CN | H | Cl | H | H | 76 |
| 24 | Cl | Cl | H | H | H | 63 |

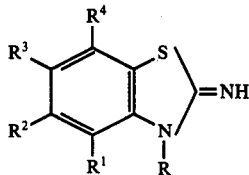

| Example | R¹ | R² | R³ | R⁴ | R | Yield (%) |
|---|---|---|---|---|---|---|
| 25 | OCH₃ | H | Br | CH₃ | H | 92 |

We claim:

1. A process for the manufacture of benzothiazoles from an N-phenylthiourea of the formula

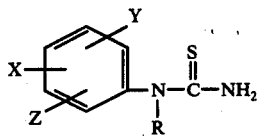

where X is hydrogen, chlorine, bromine, alkyl of 1 to 4 carbon atoms, alkoxycarbonyl of 1 to 4 carbon atoms, alkoxy of 1 to 4 carbon atoms or phenoxy, Y is hydrogen, chlorine, nitro, alkyl of 1 to 4 carbon atoms, alkoxy of 1 to 4 carbon atoms, acetylamino, benzoylamino, methylsulfonyl, ethylsulfonyl, cyano, alkoxycarbonyl (where alkoxy is of 1 to 4 carbon atoms) or sulfamoyl which may or may not be substituted by alkyl of 1 to 4 carbon atoms, Z is hydrogen, chlorine, alkyl of 1 to 4 carbon atoms or alkoxy of 1 to 4 carbon atoms and R is hydrogen, alkyl of 1 to 8 carbon atoms, benzyl or phenylethyl, by oxidative ring closure to produce a benzothiazole of the formula II

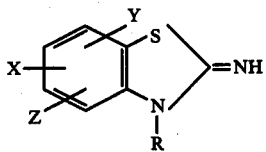

in which X, Y, Z and R have the above meanings, said process comprising contacting and reacting said N-phenylthiourea with chlorine in an aprotic organic solvent in which said N-phenyl-thiourea is dissolved or suspended and in the presence in the reaction mixture of a catalytic amount of bromine or iodine.

2. A process as claimed in claim 1 wherein the reaction is carried out at a reaction temperature in the range of 0° to 80° C. while passing chlorine into the reaction mixture.

3. A process as claimed in claim 2, wherein, after the chlorine is passed into the reaction mixture, said mixture is heated for 1 to 2 hours at a temperature in the range of 50° to 150° C.

4. A process as claimed in claim 1 wherein X is hydrogen, chlorine, methyl, ethyl, methoxy, ethoxy, propoxy, butoxy, or phenoxy and R is hydrogen, alkyl of 1 to 4 carbon atoms, benzyl or phenylethyl.

5. A process as claimed in claim 1 wherein the catalytic amount of bromine or iodine in the reaction mixture is an amount in the range of about $10^{-3}$ to $10^{-3}$ mol of bromine or iodine per mol of said N-phenylthiourea.

6. A process as claimed in claim 1 wherein the total amount of chlorine provided in the reaction mixture is in the range of 1 to 1.2 moles of chlorine per mol of said N-phenylthiourea.

7. A process as claimed in claim 1, wherein a catalytic amount of bromine is present in the reaction mixture.

8. A process as claimed in claim 1 wherein a catalytic amount of bromine is present in the reaction mixture, said catalytic amount being in the range of $10^{-3}$ to $10^{-1}$ moles of bromine per mol of said N-phenylthiourea.

UNITED STATES PATENT AND TRADEMARK OFFICE
CERTIFICATE OF CORRECTION

PATENT NO. : 4,113,732
DATED : September 12, 1978
INVENTOR(S) : Hans-Joachim Opgenorrh et al It is certified that error appears in the above—identified patent and that said Letters Patent are hereby corrected as shown below:

Col. 6, line 17, "N-phenyl-thiourea" should read --N-phenylthiourea--.

Col. 6, line 34, "$10^{-3}$ to $10^{-3}$" should read --$10^{-3}$ to $10^{-1}$--.

Signed and Sealed this

Fifth Day of December 1978

[SEAL]

Attest:

RUTH C. MASON
Attesting Officer

DONALD W. BANNER
Commissioner of Patents and Trademarks